United States Patent [19]

Ong

[11] 3,976,069

[45] Aug. 24, 1976

[54] INJECTION SYRINGE WITH CARTRIDGE RETAINING TAB

[75] Inventor: Daniel Ong, Eindhoven, Netherlands

[73] Assignee: U.S. Philips Corporation, New York, N.Y.

[22] Filed: Mar. 31, 1975

[21] Appl. No.: 563,565

[30] Foreign Application Priority Data
Apr. 8, 1974   Netherlands .................. 7404736

[52] U.S. Cl. ................. 128/218 D; 128/218 DA
[51] Int. Cl.² .................................... A61M 5/00
[58] Field of Search ..... 128/218 D, 218 DA, 218 R, 128/220, 221, 215, 216, 224, 260, 261

[56] References Cited
UNITED STATES PATENTS

| | | | |
|---|---|---|---|
| 2,778,359 | 1/1957 | Friedman .................. | 128/218 D |
| 2,834,346 | 5/1958 | Adams ..................... | 128/218 R |
| 2,994,323 | 8/1961 | Dann et al. ................ | 128/218 D |
| 3,110,309 | 11/1963 | Higgins ................... | 128/218 D |

*Primary Examiner*—John D. Yasko
*Attorney, Agent, or Firm*—Frank R. Trifari; David R. Treacy

[57] ABSTRACT

An injection syringe having a cartridge with an injection needle, and a cartridge holder. The holder is provided with resilient tabs which at one end are connected at an acute angle to the inner surface of the holder, and for the remaining part are clear of the cartridge holder. The free end engage a neck portion of the cartridge, thereby locking the cartridge in the holder.

5 Claims, 3 Drawing Figures

U.S. Patent   Aug. 24, 1976   3,976,069

INJECTION SYRINGE WITH CARTRIDGE RETAINING TAB

BACKGROUND OF THE INVENTION

1. Field of the Invention

The invention relates to an injection syringe which is provided with a cartridge holder and a cartridge. The cartridge holder is a substantially circular cylindrical hollow body which at one end, the rear, is provided with a grip and the other end is provided with projections on its inner surface. The cartridge is also a substantially circular cylindrical hollow body whose outer diameter is slightly smaller than the inner diameter of the cartridge holder so that the cartridge can be accommodated in the holder. At the front the cartridge has an injection needle, and an adjoining constriction or neck. The projections of the cartridge holder engage the neck of the cartridge and thus secure the cartridge in the holder.

2. Description of Prior Art

Injections syringes of this type are known from the Applicant's Netherlands Patent Specification 133,649 or the corresponding British Pat. specification 1,204,709.

In said known constructions the projections consist of cams which are integral with the cylindrical wall of the cartridge holder. The material of the cartridge holder, and thus of the cams, is slightly elastic. Upon insertion of a cartridge, which is provided with a collar and a neck adjoining said collar, into the holder provided with cams, the collar presses the cams slightly outwards so that the collar can pass the cams. After the passage of the collar the cams spring back into the neck portion of the cartridge and thus secure the cartridge in the holder. Such a construction has the drawback that a substantial force is required to obtain the desired radial displacement of the cams, because the applied force must be capable of causing radial expansion of the cylindrical wall of the holder over the circumference of said cylindrical wall at the location of the cams. Practical tests have revealed that automatic insertion of the cartridge into the holder frequently causes breakage of the cartridge. Furthermore, it has been found that after radial displacement the cams in some cases do not entirely spring back into their original position, so that no satisfactory locking is achieved. The dimensions of the cams and the collar must be very accurately adapted to each other, which makes the construction very expensive.

It is also known from U.S. Pat. No. 2,695,613 to provide cartridges with a detachable needle, the needle comprising a grip with resilient arms in which tablike elements are blanked out. This device, however, is not concerned with the problem of non-detachably securing a cartridge in a rigid construction of a cylindrical closed holder.

SUMMARY OF THE INVENTION

According to the invention, projections on a cartridge holder consist of resilient tabs which are connected at one end to the inner surface of the cartridge holder, and for the remaining part are clear of the cartridge holder and which furthermore enlose an acute angle with the front part of the cartridge holder.

During assembly of the injection syringe according to the invention, the cartridge, whose injection needle is preferably protected by a needle guard, is inserted into the cartridge holder via the rear of the holder. The collar of the cartridge then butts against the resilient tabs or tab-like elements, which as a result of the force exerted on them are moved against the inner wall of the holder, so that the collar can pass the tabs. After passage no more radial forces is exerted on the tabs, so that they can return to the original position, thereby engaging the neck of the cartridge. In the normal, i.e. unloaded position, the tabs make an acute angle with the frontmost part of the holder. The tabs thus assume an oblique forward position, so that it is not possible to remove the cartridge via the rear after it has been inserted in the holder. Giving the cartridge beyond the neck portion a slightly greater outer diameter than that of the collar ensures that the cartridge can not be removed from the holder via the front. The part of the cartridge with the increased outer diameter then cannot pass the tabs. It is equally possible to provide the cartridge holder at the front with an inwardly disposed stop shoulder or with one or more cams, which prevent removal of the cartridge from the holder via the front.

The force with which the resilient tab-like elements are pressed against the wall of the holder is small, so that upon insertion of the cartridge into the holder the risk of breakage of the cartridge, which is preferably made of glass, is nil or minimal. Owing to the easy radial displacement of the resilient tab-like elements the dimensioning of said tabs and thus the spacing of the free ends of the tabs to the inner wall of the holder is non-critical. This renders the construction inexpensive and has the additional advantage that even though the tabs after passing the collar of the cartridge do not completely return to their original position, it is still possible to obtain satisfactory locking.

In a preferred embodiment of the injection syringe according to the invention the inner surface of the cartridge holder is provided with a multiplicity of longitudinal ribs which at the front ends are provided with the resilient tab-like elements. Said parallel ribs, which extend in the longitudinal direction of the cartridge holder, are preferably spaced at regular intervals over the circumference of the cartridge holder. The number of ribs is variable, but is preferably three. The ribs act as guide ribs and facilitate the insertion of a cartridge into the holder. During insertion the collar of the cartridge presses the resilient tab-like elements against the wall of the holder so that they form an extension of the ribs.

In a further preferred embodiment of the injection syringe according to the invention the front part of the holder which extends as far as the resilient tab-like elements comprises a thickened wall portion, the internal diameter of said portion being smaller than that of the rear portion of the cartridge holder which is situated beyond the tab-like elements.

In the thickened wall portion the collar of the cartridge at the outer circumference is gripped in such a way that a torque can be taken up which suffices to twist off a needle guard which is disposed over the needle of the cartridge. Furthermore, the thickened wall portion constitutes a stop for the part of the cartridge is disposed behind the neck, so that a further axial displacement of the cartridge in a forward direction is thereby prevented.

BRIEF DESCRIPTION OF THE DRAWING

The invention will be explained in more detail with reference to the drawing, in which.

DESCRIPTION OF THE PREFERRED EMBODIMENTS

Figure 1:
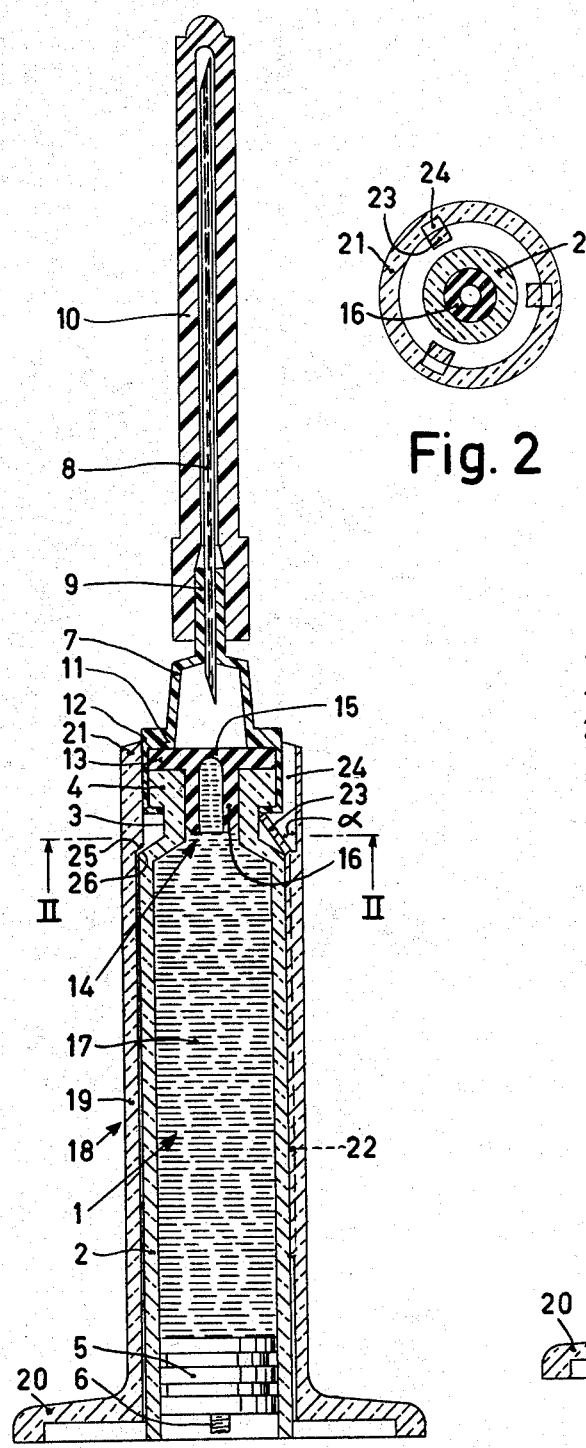
FIG. 1 is a longitudinal section of an injection syringe according to the inventon.
Figure 2:
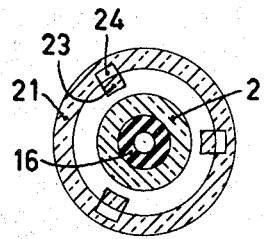
FIG. 2 is a cross-section taken on the line II-II in FIG. 1.

In the drawing 1 denotes a cartridge which, is for example, made of glass. The cartridge is a substantially circular cylindrical body which at the front end comprises a neck 3 with a flange 4. The outer diameter of flange 4 is smaller than the outer diameter of the cylindrical body 2. At the lower end the cartridge is closed by a plunger 5 which is movable inside the cartridge, which plunger is provided with a threaded member 6. On the threaded member 6 a plunger rod may be screwed which is not shown in the drawing. At the front the cartridge 1 is provided with a metal (Al) or plastic needle mount 7 having an injection needle 8 which is bevelled at both ends. The injection needle 8 is secured in a cylindrical sleeve 9 of the needle mount 7. Around the injection needle a needle guard 10 is disposed, the guard being frictionally clamped on the sleeve 9. The needle mount 7 comprises a flange portion with collar 12 having an outer diameter less than that of the cylindrical body 2. By means of collar 12 the needle mount 7 is clamped onto the front face of the cartridge 1, a flange 13 of a stopper 14 which is for example made of rubber being disposed between the flange 4 of the cartridge and the flange portion 11 of the needle mount. The stopper 14 is provided with a diaphragm 15 and a neck 16. Between the plug 14 and the plunger 5 a liquid medicament 17 is contained.

Cartridge 1 is disposed in a cartridge holder which is generally denoted by the reference numeral 18. The cartridge holder 18 is a substantially cylindrical body 19 which at one end (rear) is provided with a grip 20 and at the other end (front) comprises a thickened wall portion 21. The inner diameter of wall portion 21 is smaller than that of the body 19. Furthermore, the inner diameter of wall portion 21 is adapted to the outer diameter of the collar 12 in such a way that the collar 12 is frictionally secured in the wall portion 21. The frictional force suffices to withstand the twisting torque needed for removal of the needle guard 10.

The inner surface of body 19 is provided with three axial guide ribs 22 which are disposed at regular intervals over the circumference, the front ends of said ribs being provided with resilient tabs 23. Each tab is connected at a rear edge to a rib 22 and for the remaining part it is clear of the wall of cartridge holder 18. The tab 23 makes an acute angle α with wall portion 21 and engages neck 3 of cartridge 1 with the free end. Wall portion 21 at the location of each tab element 23 is provided with an axial slot 24 which during radial displacement of the element 23 can partly or completely accommodate said element.

Figure 3:
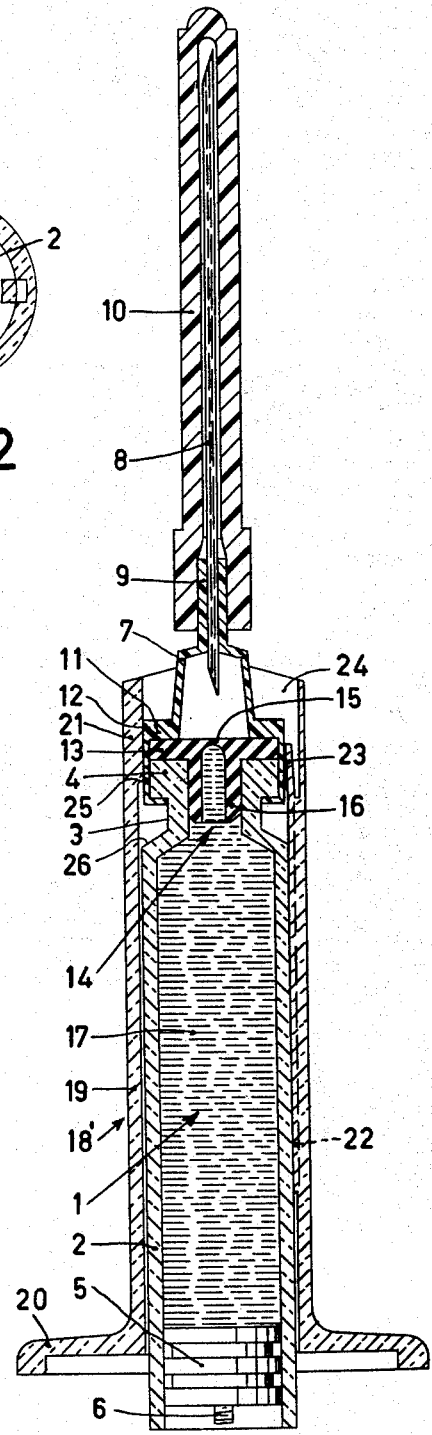
FIG. 3 is a longitudinal section of an injection syringe according to the invention during assembly.

During assembly of the injection syringe according to the invention the cartridge 1 is inserted into the holder 18 via the rear (19,20) of the holder. Due to the presence of guide ribs 22 the cartridge can be readily inserted. Collar 12, during insertion of the cartridge, will rub against the obliquely forward tab 23 and exert a radial outwardly disposed force on them. Under the influence of said force the tab elements are radially moved and are accommodated in the slots 24 of wall portion 21. The collar 12 can now pass the elements 23. The situation in which collar 12 has partly passed the elements 23 is shown in FIG. 3. When, upon further insertion of the cartridge, the collar 12 no longer exerts a force on the elements 23, said elements will return to the original position and thereby engage the neck 4 of cartridge 1 (FIG. 1). Further axial displacement of the cartridge 1 in the forward direction is not possible because the rim 25 of wall portion 21 constitutes a stop for the shoulder 26 of cartridge 1. Axial movement of the cartridge to the rear is not possible either because of the tabs 23 which are disposed obliquely forwardly and which engage with the neck 4 of the cartridge 1. Collar 12 of cartridge 1 can pass the tabs 23 in one direction only, viz. axially forwards.

When using an injection syringe according to the invention the plunger is moved forwards with the aid of a plunger rod which is screwed onto member 6. The pressure exerted on the medicament 17 causes the diaphragm 15 to bulge up and subsequently to burst either spontaneously or upon contact with the bevelled injection needle 8. After removal of the needle guard the injection syringe is ready for application.

What is claimed is:

1. An injection syringe having a cartridge and a cartridge holder, the cartridge comprising a substantially circular cylindrical body having an outer diameter, a front end, an injection needle, and means for holding said needle at a front end of said body, said body having a circumferential restriction adjacent said front end and an axially and radially extending flange beyond said restriction; the cartridge holder comprising a substantially circular cylindrical hollow body having a rear portion having a grip, and a front end having a number of inward projections, said cylindrical body having an inner wall having inner diameter greater than said outer diameter, adapted to receive a cartridge therein; wherein said inward projections are a plurality of resilient tabs extending away from said rear portion obliquely inwardly at an acute angle with respect to said inner wall, and having a rear edge connected to said inner wall, and said holder comprises means for allowing said tabs to be deflected outward upon insertion of a cartridge into the holder from the rear, said tabs being adapted to spring inward and engage said restriction upon complete insertion of a cartridge.

2. A syringe as claimed in claim 1, wherein said holder inner wall has a plurality of inwardly projecting guide ribs, said tabs extending from forward ends of said ribs.

3. A syringe as claimed in claim 2, wherein said means for allowing comprises a respective plurality of grooves in said inner wall outward of said tabs.

4. A syringe as claimed in claim 1, wherein said front end of said holder comprises a section having a thickened wall portion, said wall portion having an inside diameter less than that of the portion of the body to the rear of the tabs.

5. A syringe as claimed in claim 4, comprising in addition a removable needle guard, and wherein said means for holding said needle comprises a mount made of material more resistant to breaking than the circular cylindrical body, a portion of said mount enclosing said flange, said thickened wall portion engaging said portion of said mount with sufficient frictional force to permit removal of said needle guard without movement of the cartridge with respect to the holder.

* * * * *